United States Patent [19]

Watson et al.

[11] Patent Number: 4,563,517

[45] Date of Patent: * Jan. 7, 1986

[54] POLYMER MODIFICATION SYSTEM FOR VINYLAROMATIC MONOMER PRODUCTION APPARATUS

[75] Inventors: James M. Watson; James R. Butler, both of Big Spring, Tex.; Mark Victor, Catonsville, Md.

[73] Assignee: Cosden Technology, Inc., Dallas, Tex.

[*] Notice: The portion of the term of this patent subsequent to Jun. 5, 2001 has been disclaimed.

[21] Appl. No.: 488,970

[22] Filed: Apr. 13, 1983

Related U.S. Application Data

[63] Continuation of Ser. No. 248,474, Mar. 27, 1981, Pat. No. 4,452,975.

[51] Int. Cl.[4] ............................................. C08F 6/00
[52] U.S. Cl. .................................... 528/493; 528/496; 528/497; 528/500
[58] Field of Search ................. 134/30, 22 R; 528/480, 528/493, 484, 496, 497, 499, 500; 585/440, 441

[56] References Cited

U.S. PATENT DOCUMENTS

| | | | |
|---|---|---|---|
| 2,749,313 | 6/1956 | Williams | 528/484 |
| 2,801,234 | 7/1957 | Hanson | 528/484 |
| 3,004,014 | 10/1961 | Myerholtz, Jr. | 526/346 |
| 3,255,166 | 6/1966 | Bernhardt | 528/493 |
| 3,558,576 | 1/1971 | Weller | 528/493 |
| 3,657,162 | 4/1972 | Finestone | 526/86 |
| 3,705,190 | 12/1972 | Bockstahler | 528/484 |
| 3,764,384 | 10/1973 | Berni | 528/484 |

*Primary Examiner*—Christopher A. Henderson
*Attorney, Agent, or Firm*—John K. Abokhair; M. Norwood Cheairs

[57] ABSTRACT

Disclosed is a process for modifying accumulated cross-linked polymer in an apparatus used for the production of a vinylaromatic compound, comprising optionally softening the polymer with an organic solvent; precipitating the polymer with a light, polar non-solvent for the polymer and expanding the softened polymer by bringing the softened polymer in contact with steam whereby the polymer is converted into a state which enables it to be more easily removed from the apparatus.

3 Claims, 1 Drawing Figure

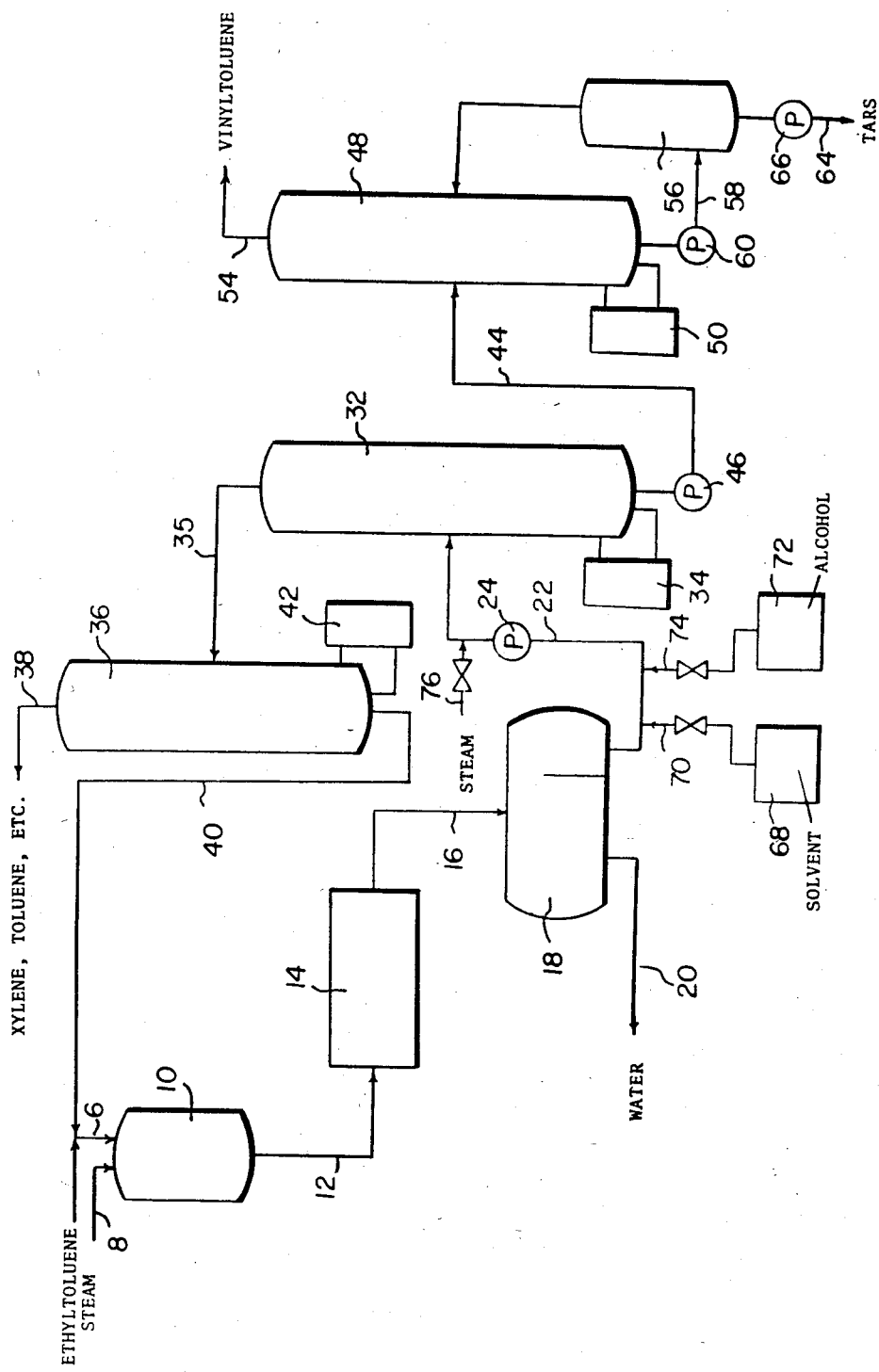

POLYMER MODIFICATION SYSTEM FOR VINYLAROMATIC MONOMER PRODUCTION APPARATUS

RELATED APPLICATIONS

This application is a continuation of the parent application filed Mar. 27, 1981, with Ser. No. 248,474, and now issued as U.S. Pat. No. 4,452,975.

BACKGROUND OF THE INVENTION

The present invention relates to a process for the production of readily polymerizable vinylaromatic compounds. More particularly, the present invention relates to a process for the removal of polymers which collect in the apparatus utilized in the production of vinylaromatic compounds.

It is well known that monomeric styrene, vinyltoluene, alkylated styrene, divinylbenzene, and other vinylaromatic compounds polymerize very readily, and furthermore, that the rate of polymerization increases at elevated temperatures. Since vinylaromatic compounds, produced by common industrial methods, contain impurities, these compounds must be subjected to separation and purification processes in order to be suitable for most types of further industrial use. Such separation and purification is generally accomplished by distillation.

In order to prevent polymerization of vinylaromatics during distillation, various types of known polymerization-inhibitors have been employed in connection with prior art distillation processes. Only a very few of these compounds have proved to be of any utility for inhibiting polymerization under distillation conditions, and even fewer are effective in the columns of the distillation apparatus.

The cross-linked polymer which may collect in the production apparatus is a hard material insoluble in ordinary solvents such as benzene or carbontetrachloride. The problem is particularly acute in, for example, the recycle columns of the distillation apparatus. The progressive growth of such deposits not only reduces the effective yield of commercial vinylaromatic monomer production processes, but also fouls lines, pumps, fractionators and other distillation equipment, thereby reducing the run length of the production apparatus and increasing the production cost of the desired vinylaromatic monomer. As these polymer deposits are insoluble, cleaning of the production equipment has required manually chipping the hard polymer out of the clogged apparatus.

Though efforts directed toward the reduction and elimination of polymer buildup show promise, it is not yet possible to completely avoid polymer buildup over periods of prolonged operation. Thus, there exists a strong need for an improved process for removing the insoluble polymer for vinylaromatic compound production apparatus.

SUMMARY OF THE INVENTION

It is therefore an object of the present invention to provide an improved method for removing insoluble cross-linked polymer from the equipment used to produce vinylaromatic compounds.

It is also an object of the present invention to provide an improved method for cleaning distillation equipment in which insoluble polymer has collected.

A further object of the invention lies in the provision of a method for physically modifying the insoluble polymer, thereby rendering it more easily removable.

Still a further object of the present invention is to provide a process for modifying insoluble polymer which uses a material having relatively low toxicity.

A specific object of the invention resides in a method for reducing the down-time required to clean a vinylaromatic compound production apparatus, particularly apparatus for producing vinyltoluene.

In accomplishing the foregoing objects, there has been provided in accordance with the present invention a process for physically modifying accumulated cross-linked polymer in an apparatus used for the production of a vinylaromatic compound, comprising the steps of precipitating the polymer with a light polar compound and expanding the precipitated (nucleated) polymer by bringing the polymer in contact with steam. Optionally, the polymer may first be softened by treating it with an organic solvent before the precipitation treatment.

Preferably, this process further comprises the step of breaking the expanded polymer to remove the expanded polymer from the apparatus. In preferred embodiments, the organic solvent is xylene, toluene or ethyltoluene; the light, polar compound is an alcohol having from 1 to 4 carbon atoms; e.g., ethanol or a ketone; e.g., acetone or methylethylketone, and the vinylaromatic compound is vinyltoluene.

In accordance with another aspect of the invention, the optional softening step comprises contacting the polymer with refluxing organic solvent, and the precipitating step comprises contacting the polymer with refluxing alcohol.

Through the use of the process of the present invention, the cross-linked polymer which collects in apparatus used for the production of vinylaromatic compounds may be modified to form an expanded polymer. This modified polymer is much more easily broken and removed from the apparatus than is the unmodified polymer. By utilization of the process of the invention, the removal of polymer accumulations is thus greatly facilitated, and the time required for such removal is reduced accordingly.

BRIEF DESCRIPTION OF THE DRAWING

The invention will be explained in further detail with reference to the accompanying drawing which is a schematic representation of a system in which the process of the invention may be utilized.

DETAILED DESCRIPTION OF PREFERRED EMBODIMENTS

The vinylaromatic polymer modification system of the invention is especially adapted for use in the production equipment of vinylaromatic monomers, especially vinyltoluene. The process of the present invention changes the hard, glassy, cross-linked polymer which accumulates in the process equipment into an expanded, brittle polymer which may easily be fractured and removed. The polymer modification system disclosed may be used in the production apparatus to be cleaned, essentially without necessitating the alteration of that equipment.

The process of the invention will now be illustrated in the context of process equipment for the production of vinyltoluene, though it will be understood that this process is equally applicable to the process equipment used in the production of other vinylaromatic compounds, such as styrene, divinylbenzene, alpha-methylstyrene and the like.

Referring to the drawing, the figure illustrates an apparatus used in the production of vinyltoluene. In an illustrative vinyltoluene production process, an ethyltoluene feedstock and steam are introduced through lines 6 and 8 respectively into a dehydrogenation apparatus 10 and reacted in the presence of a suitable catalyst to form vinyltoluene. The vinyltoluene product stream is withdrawn via line 12 and condensed in a condenser 14, then transferred via line 16 to separator 18. Condenser 14 may comprise any of the known types of condensing apparatus using water, air, heat exchange with other process fluids, or a combination of two or more of the foregoing to effect condensation.

The aqueous phase of the vinyltoluene product stream is separated from the crude vinyltoluene organic phase in the separator. The aqueous phase is withdrawn through line 20 and is recycled for water treatment and use in the boilers used in the dehydrogenation of ethyltoluene.

The crude organic product phase from separator 18 is pumped through line 22 via pump 24 into the vinyltoluene distillation train.

In this apparatus, the crude vinyltoluene is introduced into the intermediate portion of recycle column 32 which is preferably of parallel distillation path design. Reboiler 34 provides the necessary heat for distillation in column 32.

An overhead product comprising ethyltoluene and lower boiling components such as toluene, benzene, xylene, ethylbenzene and nonaromatics is withdrawn through line 35 for subsequent fractionation in distillation column 36. In column 36, toluene, xylene and other light distillates are separated and withdrawn through line 38. An ethyltoluene bottoms product is withdrawn through line 40 and is recycled for use in the ethyltoluene dehydrogenation reactor 10. Reboiler 42 provides the bottoms with the necessary heat for the distillation.

The recycle bottoms product, containing vinyltoluene inhibitor and polyvinyltoluene is withdrawn from the recycle column 32 through line 44 using pump 46 and is charged into the middle portion of finishing column 48. A reboiler 50 is attached to finishing column 48 for supplying the necessary heat within the column. The purified vinyltoluene overhead product is withdrawn through line 54.

The finishing column bottoms product is directed to flash pot 56 via line 58 and pump 60. The flash pot 56 has a reboiler 62 to facilitate the fractionation of the bottoms. The tar produced during the distillation process is withdrawn through line 64 by pump 66 for proper disposal.

The recycle column 32 is particularly susceptible to polymer buildup. When polymer buildup is sufficient to require the cleaning of the recycle column 32, the hydrocarbon inventory in the column is removed, and a light, polar compound which is substantially a nonsolvent for the polymer, such as an alcohol having from 1 to 4 carbon atoms or a ketone such as acetone or methylethylketone is introduced into the recycle column 32 from supply tank 72 through line 74 and line 22. A preferred light, polar compound is ethanol, because of its relatively low toxicity. The use of methanol is not preferred because it poses possible health hazards. This factor is especially important due to the hand labor necessary to fracture and remove the polymer from the column, and the resultant exposure of maintenance personnel to any residual alcohol remaining in the modified polymer.

The alcohol is preferably refluxed in column 32 by means of reboiler 34 until the alcohol has sufficiently precipitated the polymer. The alcohol reflux is maintained for a time from about 2 to about 100 hours, preferably from about 10 to about 50 hours. The alcohol is then withdrawn by means of line 35. Treatment with hot alcohol may be used in equipment where a reflux is not feasible.

Following the precipitation of the polymer, a flow of steam is introduced into the recycle column 32 by means of lines 76 and 22. The steam expands the precipitated polymer, and also tends to remove most of the free alcohol and solvent from the polymer. To assist in removal of hydrocarbons from the column in order to make it safe for human entry, the steam treatment may be periodically interrupted by a water wash of the column. After a suitable time, usually from about 1 to about 72 hours, and preferably from about 10 to about 48 hours, the steam treatment is discontinued. After cooling, the expanded polymer may be easily broken into manageable pieces and removed from the equipment.

If desired, the polymer accumulations may initially be subjected to an optional softening treatment before being treated with the light, polar compound. An organic solvent which can soften the polymer is introduced from solvent source 68 through line 70 into line 22 and fed into the recycle column 32. Suitable solvents include toluene, xylene, xylene bottoms, ethyltoluene and other similar solvents. The use of xylene, toluene or ethyltoluene is preferred. Reboiler 34 provides the heat necessary to maintain a reflux of the solvent within the column. The reflux is maintained for a time from about 5 to about 100 hours, preferably from about 10 to about 50 hours, after which the solvent is drawn off through line 35. When the process is applied to lines and other process equipment in which reflux is not practical, heated solvent may be used to bathe the accumulated polymer for an appropriate length of time.

In order to more fully describe the present invention, the following illustrative examples are presented.

EXAMPLE I

Samples of polymer taken from the recycle column of a vinyltoluene distillation train were refluxed in a 200 ml flask in toluene for 7 hours. The toluene was decanted, and replaced with ethanol. The samples of polymer were then refluxed in ethanol for 3 hours. After removal of the ethanol, the samples were steamed for 3 hours. The original hard polymer, having a density of about 1.2 g/cc, had expanded into a modified polymer having a density of about 0.75 g/cc. The modified polymer exhibited a porous structure and was readily crushed.

EXAMPLE II

Following a vinyltoluene production run in which a significant amount of cross-linked polymer was known to have accumulated in the recycle column of the distillation train, the distillation system was drained of hydrocarbons. The recycle column was washed with ethyltoluene to remove polymerizable monomer and was subsequently inventoried with xylene. The xylene was heated at reflux with the pressure on the column being adjusted to maintain a bottoms temperature of approximately 220 degrees F. for approximately 48 hours, and the column was then cooled and drained.

Vacuum was broken and the column was inventoried with ethanol and heated at reflux for approximately 48 hours. The system was again cooled and drained, and the ethanol was saved for reuse. The column was subsequently steamed for approximately 72 hours to effect density adjustment of polymer and to remove ethanol vapors.

Upon subsequent entry of the column for mechanical removal of the accumulated polymer, the texture of the polymer deposits was found to be porous and the mechanical strength greatly reduced in comparison to similar polymer which had been found after previous runs. As a consequence, the number of manhours required for polymer removal was reduced by a factor of approximately 50%.

EXAMPLE III

At the end of a vinyltoluene production run the recycle column of the distillation train used to purify the crude vinyltoluene was shut down as follows. The hydrocarbon mixture remaining in the column comprising principally vinyltoluene and ethyltoluene was drained from the column and stored. Ethyltoluene was introduced into the column and refluxed for a short period of time to assure removal of residual vinyltoluene. The ethyltoluene was then drained from the column and combined with the stored material drained from the column at the end of the run. The stored material will be reprocessed when the recycle column is restarted for the next production run, to reclaim the vinyltoluene and ethyltoluene. Ethanol is then introduced into the column and refluxed for at least 72 hours after which the ethanol is pumped back to the ethanol storage tanks for subsequent reuse. The column is then alternately steamed for periods of 4 hours and washed with water for periods of about 1 hour for a total of about 48 hours until hydrocarbon levels in the column were sufficiently reduced to make the column safe for human entry. Polymer accumulations were then manually removed from the interior of the column. As a result of the treatment, the normally dense, hard polymer accumulations were found to be somewhat porous and brittle, and removal of the polymer was greatly facilitated.

The foregoing embodiments of the invention have been set forth solely as illustrations of the invention and are not intended to be limiting. Since modifications of the disclosed embodiments within the scope and spirit of the invention may occur to persons skilled in the art, the scope of the invention is to be limited solely by the scope of the appended claims.

What is claimed is:

1. A process for modifying insoluble, cross-linked polymer accumulations in an apparatus used for the production of a vinylaromatic monomer, comprising the steps of:
    contacting the insoluble polymer accumulation with a light, polar non-solvent for the polymer; and
    thereafter expanding the accumulated polymer by subjecting the polymer to steam.

2. A process as claimed in claim 1, wherein said vinylaromatic compound is vinyltoluene.

3. A process for removing insoluble, cross-linked polymer accumulations from apparatus used in the production of vinylaromatic monomer, comprising the steps of:
    subjecting said insoluble polymer accumulation to a refluxing light, polar non-solvent for the polymer for a period of from about 2 to about 100 hours; and
    thereafter expanding the accumulated polymer by subjecting said polymer to steam for a period from about 1 to about 72 hours,
    whereby said polymer is modified to become more easily mechanically removable.

* * * * *